(12) United States Patent
Johnson

(10) Patent No.: US 6,440,415 B1
(45) Date of Patent: Aug. 27, 2002

(54) ODOR ELIMINATING ITEMS AND METHODS OF USE FOR HUNTING

(75) Inventor: Louis B. Johnson, Troy, AL (US)

(73) Assignee: Johnson Laboratories, Inc., Troy, AL (US)

( * ) Notice: Subject to any disclaimer, the term of this patent is extended or adjusted under 35 U.S.C. 154(b) by 0 days.

(21) Appl. No.: 09/574,208

(22) Filed: May 19, 2000

Related U.S. Application Data

(60) Provisional application No. 60/139,760, filed on May 28, 1999.

(51) Int. Cl.$^7$ ................................................ A61K 33/44
(52) U.S. Cl. ..................... 424/125; 424/46; 424/76.1; 424/76.21; 424/715; 424/717
(58) Field of Search .................. 424/125, 405, 424/421, 43, 46, 47, 76.1, 76.21, 76.9, 717, 718; 106/286.6, 286.8; 252/183.16

(56) References Cited

U.S. PATENT DOCUMENTS

| | | | |
|---|---|---|---|
| 3,586,596 A | | 6/1971 | Ainsworth et al. |
| 4,181,712 A | | 1/1980 | Rialdi |
| 4,833,181 A | | 5/1989 | Narukawa et al. |
| 5,197,208 A | | 3/1993 | Lapidus |
| 5,383,236 A | | 1/1995 | Sesselmann |
| 5,429,628 A | * | 7/1995 | Trinh et al. ................. 604/359 |
| 5,539,930 A | | 7/1996 | Sesselmann |
| 5,780,020 A | | 7/1998 | Peterson et al. |
| 5,790,987 A | | 8/1998 | Sesselmann |
| 5,861,144 A | | 1/1999 | Peterson et al. |
| 5,874,067 A | | 2/1999 | Lucas et al. |
| 5,882,638 A | | 3/1999 | Dodd et al. |
| 5,885,599 A | | 3/1999 | Peterson et al. |

FOREIGN PATENT DOCUMENTS

| | | | |
|---|---|---|---|
| EP | 0392528 | * | 10/1990 |
| GB | 2169276 | * | 7/1986 |
| JP | 55-132619 | * | 10/1980 |
| JP | 55132619 | * | 10/1980 |

OTHER PUBLICATIONS

U.S. Army Natick Research, Development and Engineering Center, Military Specification—Cloth, Laminated, Nylon Tricot Knit, Polyurethane Foam Laminate, Chmical Protective and Flame Resistant, Sep. 17, 1981.

"Disappearing Act!", Advertisement in Buckmasters Whitetail Magazine, Sep. 1991.

"The Hunter's Edge Story", Edge Outfitters, Sep. 1991.

* cited by examiner

Primary Examiner—Neil S. Levy
(74) Attorney, Agent, or Firm—Clark & Brody

(57) ABSTRACT

A regimen for hunting includes using a number of activated carbon-containing personal items in connection with a hunter's apparel and body to reduce the hunter's scent for improved hunting. The personal items include mouthwash, deodorant/antiperspirant, body and boot powder, bar and liquid soap for cleansing the body and hair, laundry detergent and dryer sheets. Each of the personal items includes an effective amount of activated carbon, so that use of the personal items reduces the available scent to be detected by animals in the wild.

2 Claims, No Drawings

ODOR ELIMINATING ITEMS AND METHODS OF USE FOR HUNTING

This application claims benefit of Serial No. 60/136,760, filed May 28, 1999.

FIELD OF THE INVENTION

The present invention is directed to odor eliminating items and methods of use, and in particular to personal items using activated carbon for use prior to or during hunting.

BACKGROUND ART

In the prior art, the use of activated carbon or charcoal on hunting clothes or other hunting-related apparel for masking the scent of a hunter is known. U.S. Pat. No. 5,539,930 to Sesselmann discloses such an application. This patent incorporates activated charcoal as part of a hunter'clothing to absorb human odors and prevent such odors from signaling wild game of the presence of humans.

Activated charcoal is also used in compositions for controlling malodors on human skin as described in U.S. Pat. No. 5,874,067 to Lucas et al. In this patent, the composition may optionally contain hydrophobic antimicrobials, zinc salts, activated carbon, etc. U.S. Pat. No. 5,861,144 to Peterson et al. discloses a moisture and odor absorbing powder composition which may contain additional odor controlling agents such as zeolites, activated charcoal, sodium bicarbonate, antimicrobial agents, and antiperspirants.

However, a nee still exists to further mask human odors during hunting. In response to this need, the present invention utilizes effective amounts of activated carbon to eliminate odors, particularly odors from humans as part of a hunting regimen.

SUMMARY OF THE INVENTION

It is a first object of the present invention to provide effective ways to mask human odors, especially for hunting.

A further object of the invention is an odor eliminating spray having activated carbon as a component thereof.

Yet another object of the invention is a soap, either a liquid hair and body soap or a bar soap containing effective amounts of activated carbon.

One other object of the invention is a laundry detergent, either liquid or powder, containing activated carbon in amounts effective to remove odors during washing.

Still other objects of the invention are a boot or body powder, a stick deodorant-antiperspirant, a mouthwash, or a dryer sheet or other fabric, each containing effective amounts of activated carbon for odor control.

One other object of the invention is the use of the items listed above in conjunction with hunting apparel or a hunter, either alone or in combination. Certain items may be used prior to or during hunting.

Other objects advantages of the present invention will become apparent as a description thereof proceeds.

In satisfaction of the foregoing objects and advantages, the present invention provides a regimen of treatment in preparation for hunting or during hunting. The regimen includes the use of one or more personal items as each relates to the hunter, and the use of a number of other items for treating hunting apparel.

In one mode, the invention entails a method of preparing for hunting by applying a powder containing an amount of activated carbon up to 5.0% by weight to hunting apparel to be worn for hunting. The regimen also includes washing hunting apparel in a powdered laundry detergent containing an amount of activated carbon up to 5.0% by weight or a liquid laundry detergent containing an amount of activated carbon up to 10.0% by weight. As part of the washing step, dryer sheets could be used during machine drying, wherein the dryer sheet contains an amount of activated carbon up to 5.0% by weight. A liquid spray could be applied to the hunting apparel, the spray containing an amount of activated carbon up to 5.0% by weight to the hunting apparel to be worn for hunting or being worn for hunting. One, two or all of the steps described above can be performed in preparation for hunting. Application of the spray or powder could also be done during hunting as needed.

In another mode, the method of preparing for hunting includes applying a liquid spray or a powder, each containing an amount of activated carbon up to 5.0% by weigh to at least a portion of a hunter'body prior to or during hunting. All or a portion of the hunter'body can be washed with one of a liquid or a bar soap, the liquid soap containing an amount of activated carbon up to 3.0% by weight, and the bar soap containing an amount of activated carbon up to 5.0% by weight. The hunter can use a mouthwash containing an amount of activated carbon up to 1.0% by weight, and apply a deodorant or anti-perspirant containing an amount of activated carbon up to 1.0% by weight. Any one or all of the steps relating to personal hygiene can be used. In addition, the personal hygiene steps can be combined with one or more of the steps for treating the hunting apparel.

Preferably, for the personal hygiene items, the activated carbon amount ranges between 0.1 and 2.0% by weight for the liquid soap, between 0.1 and 4.0% by weight for the bar soap and the body powder, and between 0.1 and 0.5% by weight for deodorant or antiperspirant, and mouthwash.

When treating the apparel, the activated carbon preferably ranges between 0.1 and 4.0% for the liquid spray, the liquid laundry detergent, the dryer sheet, and the powder, and between 0.1 and 5.0% for the powdered laundry detergent.

The invention also includes the items to be used for treating the apparel, namely, the powdered and liquid laundry detergent, the dryer sheets, a powder such as a boot powder, and liquid spray. The invention also encompasses the personal hygiene items of the body powder, the liquid and bar soaps, the mouthwash, and the deodorant/antiperspirant. These items have the activated carbon contents as shown above.

DESCRIPTION OF THE PREFERRED EMBODIMENTS

In one aspect of the invention, a regime of preparation is employed whereby a number of steps can be taken in preparation of hunting that will reduce or mask the odor or scent of a person intending to go hunting.

In a first aspect, one'clothes or skin could be sprayed with a liquid spray composition containing activated carbon for odor control. The base of the spray can be water with sodium carbonate or bicarbonate and/or potassium carbonate or bicarbonate. The activated carbon in the spray can range up to 5.0% by weight, more preferably between 0.1 and 4.0%.

A second aspect would be to wash one'clothes using a liquid or powder detergent containing activated carbon. When using a liquid detergent, the base could be a conventional surfactant blend such as coconut oil amide. The activated carbon in weight percent can range up to 5.0% by weight, preferably between 0.1 and 4.0%. The powdered laundry detergent can have a soda ash and sodium sulfate base, and can contain up to 10.0% by weight activated carbon, preferably between 0.1 and 5.0%.

A third aspect of the regimen would be for a hunter to use a mouthwash and/or a stick deodorant/antiperspirant prior to hunting. The mouthwash could employ water as a base and the activated carbon could range up to 1.0% by weight, preferably between 0.1 and 0.5%. The deodorant-antiperspirant can have a typical glycol base, and the amount of activated carbon can range up to 1.0% by weight, preferably between 0.1 and 0.5%.

A fourth aspect would be to dust the hunter'footwear, e.g., boots, and body with a powder. The powder can be a talc, sodium bicarbonate, and corn starch combination, and the weight percentage of activated carbon can be up to 5.0%, preferably between 0.1 and 4.0%.

A fifth aspect involves washing the hunter'skin with bar soap, washing the hunter'hair with a liquid soap, and using dryer sheets when drying the hunter'clothes. The bar soap can be a typical tropical oil base soap, and have a weight percentage of activated carbon of up to 5.0%, preferably between 0.1 and 4.0%. The liquid soap can be either an ammonium or sodium laurel sulfate or a coconut oil amide. The activated carbon weight percentage can be up to 3.0%, preferably between 0.1 and 2.0%. The dryer sheets can be impregnated with up to 5.0% by weight activated carbon, preferably between 0.1 and 4.0%.

One or a combination of the above steps can be employed as a precursor to actual hunting, or during hunting. By using activated carbon in connection with the personal items such as soaps, mouthwashes, detergents, etc., less scent is available to alert animals that hunters are nearby. With less warning to the animals, more success in hunting can be achieved.

Although activated carbon is disclosed, the carbon may be in the form of activated charcoal if desired. The charcoal amount selected would be based on the ranges of activated carbon as described above.

It should also be understood that the activated carbon could be employed in the stated amounts in other known compositions for the various items disclosed herein. The import of the invention lies in the use of activated carbon in the various items associated with the hunter and the hunter'apparel as a cumulative regimen to reduce human odors or scents. Soaps, powders, mouthwashes, deodorants/anti-perspirants, dryer sheets or other fabrics, detergents (liquid or powdered), and sprays having bases other than those disclosed above could also be modified with the effective amounts of activated carbon for scent reduction.

As such, an invention has been disclosed in terms of preferred embodiments thereof which fulfills each and every one of the objects of the present invention as set forth above and provides new and improved ways to control emanation of human odors for hunting.

Of course, various changes, modifications and alterations from the teachings of the present invention may be contemplated by those skilled in the art without departing from the intended spirit and scope thereof. It is intended that the present invention only be limited by the terms of the appended claims.

What is claimed is:

1. A hunting scent eliminating item comprising a liquid spray, the liquid spray containing an effective amount of activated carbon up to 5.0% by weight for scent elimination, wherein the liquid spray consists essentially of the base of water, the activated carbon, and the one or more of sodium carbonate, sodium bicarbonate, potassium carbonate, and mixtures of sodium carbonate or sodium bicarbonate and potassium carbonate.

2. The item of claim 1, wherein the activated carbon amount ranges between 0.1 and 4.0%.

* * * * *